United States Patent [19]
Gabel et al.

[11] Patent Number: 4,759,751
[45] Date of Patent: Jul. 26, 1988

[54] CATHETER ASSEMBLY WITH AIR PURGING FEATURE

[75] Inventors: Jonathan B. Gabel, Sayreville; Mark S. Barabas, Clifton, both of N.J.

[73] Assignee: Becton, Dickinson and Company, Franklin Lakes, N.J.

[21] Appl. No.: 911,858

[22] Filed: Sep. 26, 1986

Related U.S. Application Data

[63] Continuation-in-part of Ser. No. 795,819, Nov. 7, 1985, Pat. No. 4,714,461.

[51] Int. Cl.⁴ .............................................. A61M 1/00
[52] U.S. Cl. ..................................... 604/122; 604/256
[58] Field of Search ................ 604/122, 35, 53, 97–99, 604/124, 125, 263, 280, 283, 129, 256, 163, 411

[56] References Cited
U.S. PATENT DOCUMENTS

| 2,687,731 | 8/1954 | Iarussi et al. | 604/256 |
| 3,055,361 | 9/1962 | Ballard | 604/163 |
| 3,405,713 | 10/1968 | Solowey | 604/263 |
| 3,512,524 | 5/1970 | Drewe | 604/263 |
| 3,888,249 | 6/1975 | Stenler | 604/280 |
| 4,044,752 | 8/1977 | Patel | 604/125 |
| 4,248,223 | 2/1981 | Turner et al. | 604/122 |
| 4,312,342 | 1/1982 | Chittenden | 604/34 |
| 4,384,584 | 5/1983 | Chen | 604/98 |
| 4,465,472 | 8/1984 | Urbaniak | 604/122 |

Primary Examiner—Stephen C. Pellegrino
Attorney, Agent, or Firm—Richard J. Rodrick

[57] ABSTRACT

A catheter assembly comprises a flexible tube having a liquid-receiving lumen therethrough. The tube has a proximal end for receiving liquid into the lumen and has a closed, but penetrable, distal end. The catheter assembly also comprises an adapter which includes a body operatively, but preferably removably, positioned on the distal end of the tube. A hollow cannula is mounted in and supported by an air purging element, so that the cannula extends through a passageway in the body and through the distal end of the tube in fluid communication with the lumen. The cannula provides a path to the outside environment for purging air from the lumen as liquid is introduced into the lumen. The distal end is sealable to retain liquid within the lumen after the air purging member is removed from the tube.

6 Claims, 8 Drawing Sheets

CATHETER ASSEMBLY WITH AIR PURGING FEATURE

This application is a continuation-in-part application of Ser. No. 795,819, filed on Nov. 7, 1985, now U.S. Pat. No. 4,714,461.

BACKGROUND OF THE INVENTION

1. Field of the Invention

The present invention relates to a catheter assembly, and more particularly, concerns a catheter assembly with an air purging feature and its method of use.

2. Background Description

Catheters are used for a variety of medically related procedures. Such catheters, for example, balloon catheters, occlusion catheters, perfusion catheters, urinary and drainage catheters, and the like, often rely upon the use of an internal liquid to render the catheter functional for its desired procedure. Balloon catheters rely upon the pressure of a filling liquid to inflate or expand the balloon for the intended procedure. One such balloon catheter, known as an embolectomy/thrombectomy catheter, is utilized in the removal of blood clots from blood vessels. Representative examples of such embolectomy/thrombectomy catheters are disclosed in U.S. Pat. Nos. 4,351,341 and 3,467,101.

As the pressure of the filling liquid within the catheter increases during use, particularly if a balloon on the catheter is to be expanded, there is a possibility that the balloon may burst or the catheter tube may fail due to excess pressure of the liquid. If such bursting or failure occurs, the liquid inside the catheter will enter the blood stream of the patient. Normally, the pressurizing liquid is a saline or other physiologically inert solution which should not cause harm to the patient. However, should there be any air within the catheter, its bursting might release air into the patient's blood vessel with the possibility that an air embolus might be formed. Therefore, these catheters are typically purged of air prior to use so that only the liquid medium fills the catheter for its intended use.

It is a common technique to purge air from a catheter by creating a vacuum inside the lumen of the catheter, typically in conjunction with a syringe used for liquid filling purposes. As trapped air is released from the catheter, by a cumbersome hand manipulation and tapping procedure, the air is allowed to bubble into the syringe. The syringe is removed from the catheter in order to expel the air. Then, the syringe is reattached to the catheter filled with the liquid medium.

Such an air purging technique not only takes time, but involves a number of manipulative steps and exercises, and may require additional large size syringes other than those used for inflating the balloon. Moreover, there is a different degree of difficulty in purging air from catheters of smaller sizes or which have a construction which does not facilitate the air purging technique described above. There is, therefore, still a need for an improved air purging mechanism for those catheters which rely on a filling liquid for use. It is to such an improvement that the present invention is directed.

SUMMARY OF THE INVENTION

The catheter assembly of the present invention comprises a tube having a lumen and means for introducing liquid into the lumen. The tube has a closed distal end with means for access into the lumen. Means, operatively, but preferably removably, associated with the access means, provides a fluid path between the lumen and the outside environment for purging air from the lumen.

In one preferred embodiment of this aspect of the invention, the catheter assembly comprises a flexible tube having a liquid-receiving lumen therethrough. The tube has a proximal end for receiving liquid into the lumen and has a closed, but penetrable distal end. An air purging member includes a body removably positioned on the distal end of the tube. A hollow cannula extends through the distal end in fluid communication with the lumen. The cannula provides a path to the outside environment for purging air from the lumen as liquid is introduced into the lumen. The distal end is preferably self-sealable to retain liquid within the lumen after the member is removed from the tube.

In another aspect of the present invention, a catheter assembly kit comprises a flexible catheter tube having a lumen and means for introducing liquid into the lumen. The tube has a distal end with means for access into the lumen. Included in the kit is an air purging member having a body for removable positioning on the distal end of the tube. This purging member includes means, associated with the access means of the tube, for providing a fluid path between the lumen and the outside environment for purging air from the lumen as liquid is introduced into the lumen.

A further embodiment of the present invention is a method for purging air from a catheter having a tube with a liquid-receiving lumen. This method comprises creating a temporary fluid path between the lumen and the environment outside of the catheter. Liquid is introduced into the lumen so that the liquid travels toward the fluid path. Air is purged from the lumen through the fluid path as the liquid travels toward the fluid path. The method further includes closing the temporary fluid path subsequent to the purging of air from the lumen whereby the catheter retains the liquid inside the lumen. A valve mechanism may be employed for temporarily creating the fluid path between the lumen of the tube and the outside environment.

Another embodiment of the method of the present invention is using a liquid-filled catheter for a desired activity in a body passage. This method is substantially as described above, and further includes inserting the liquid-filled catheter into a body passage. The desired activity in the body passage is then performed with the liquid-filled catheter.

In a further embodiment of the present invention, the catheter assembly comprises a flexible tube having a liquid-receiving lumen, a proximal end for receiving liquid into the lumen and a closed, but penetrable, distal end. Air purging means includes a body removably engaged to the distal end of the tube and a hollow cannula extending through the body and the distal end in fluid communication with the lumen. The cannula provides a path to the outside environment for purging air from the lumen as liquid is introduced into the lumen. The distal end of the tube is sealable to retain liquid within the lumen after the body is removed from the tube.

A catheter kit assembly comprises a flexible catheter tube having a lumen and means for introducing liquid into the lumen. The tube has a closed distal end with means for access into the lumen. An air purging element is included for purging air from the lumen of the tube by providing a fluid path between the lumen and the outside environment. An adapter is provided for operative association between the access means and the element to facilitate the creation of the fluid path.

In accordance with the principles of the present invention, an air purging mechanism is provided as an improved alternative over the commonly known and used air purging technique. The air purging member of the present invention, and its method of use, provide an easy and effective method for purging an otherwise difficult to purge catheter. As a result of the present invention, air is easily and readily removed from the catheter so that if the catheter should burst during use, the possibility of air embolus will be eliminated or significantly reduced. Other advantages and benefits of the present invention will become more apparent upon reading the detailed description provided below.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Figure 1:
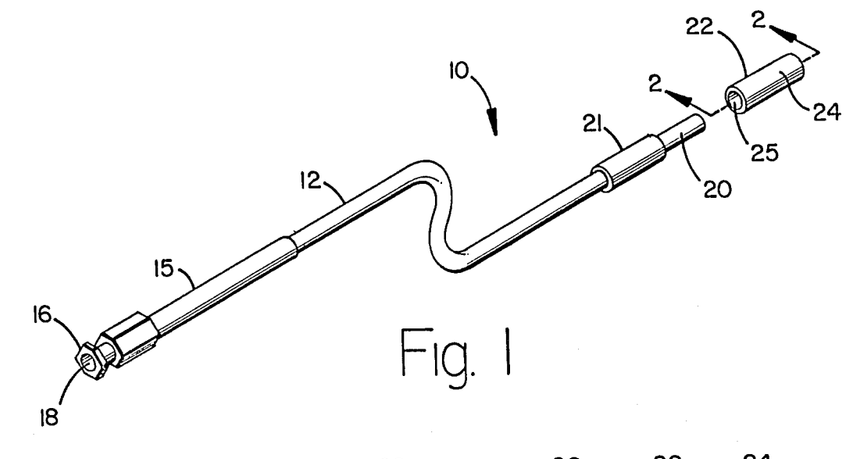
FIG. 1 is a perspective view of one embodiment of a catheter assembly of the present invention illustrating the preferred configuration of the air purging member.

Turning now to the drawings, and FIG. 1 in particular, there is illustrated a catheter assembly 10 as it may appear prior to use. Assembly 10 includes a preferably flexible catheter tube 12. This tube is preferably long and slender so as to facilitate its entry and movement into a body passage. Tube 12 is hollow and has a lumen 14 extending therethrough, as seen by briefly referring to FIG. 3. It can be seen in FIG. 1 that tube 12 has a proximal end 15, i.e., the end facing toward the user of the catheter. At the proximal end is a connector 16 which may be a conventional syringe connector to permit the coupling of a syringe for delivering filling liquid into the lumen of the tube. An opening 18 in connector 16 communicates with lumen 14 to facilitate this liquid delivery.

Tube 12 also has a distal end 20, i.e., the end facing toward the patient on whom the catheter is used. Distal end 20 may be a closed end so that liquid introduced into the lumen may be retained therein. In the embodiment being described, catheter assembly 10 is illustrated as a balloon catheter, which may be used for a variety of purposes, such as embolectomy or thrombectomy procedures, occlusion procedures, and the like within a body passage. To this end, an expandable balloon 21 is positioned at or near distal end 20. Balloon 21 is expandable by the pressure of liquid introduced into the lumen of the catheter tube. One such balloon catheter is described in the heretofore mentioned patent, U.S. Pat. No. 4,351,341. It is understood, however, that the present invention encompasses many different catheters and is not limited to the singular embodiment illustrated.

Figure 2:
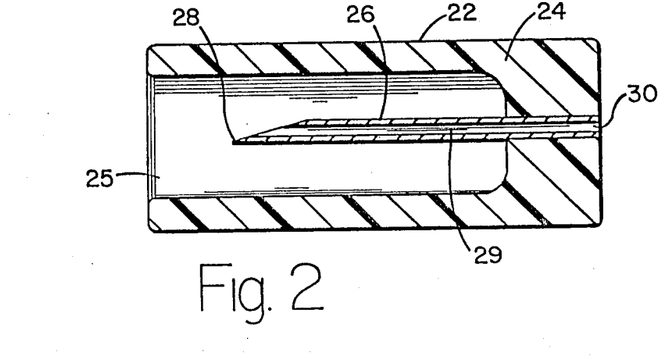
FIG. 2 is an enlarged cross-sectional view of the air purging member taken along line 2—2 of FIG. 1.

Catheter assembly 10 also includes an air purging member 22 as seen in FIGS. 1 and 2. Purge member 22 represents one preferred embodiment of the present invention and, in the embodiment being described, has a cylindrically-shaped body 24 into which a recess 25 extends along the longitudinal axis thereof. It can be seen particularly in FIG. 2 that recess 25 extends only partially through cylindrical body 24. Recess 25 is preferably shaped so that purge member 22 may slidably fit over distal end 20 of tube 12. Mounted within body 24 and preferably extending along longitudinal axis thereof is a hollow cannula 26. It is preferred that cannula 26 be mounted in body 24 so that it is substantially concentrically positioned with respect to the walls of cylindrically-shaped recess 25. Cannula 26 has a sharp point 28 and a passageway 29 extending completely therethrough. Passageway 29 thus establishes a fluid communication with recess 25 and has an open end 30 communicating with the environment outside of or external to purge member 22. It can be seen in FIG. 2 that sharp point 28 preferably, but not limitatively, lies within the confines of recess 25 so that it is protectively surrounded by body 24 of the purging member. This protective arrangement of the sharp point of the cannula prevents accidental injury to the user of the present catheter assembly. It is preferred that body 24 of the air purging member be fabricated from a rigid material, such as rigid plastic, so as to provide sufficient structural support for holding cannula 26 therein.

Figure 3:
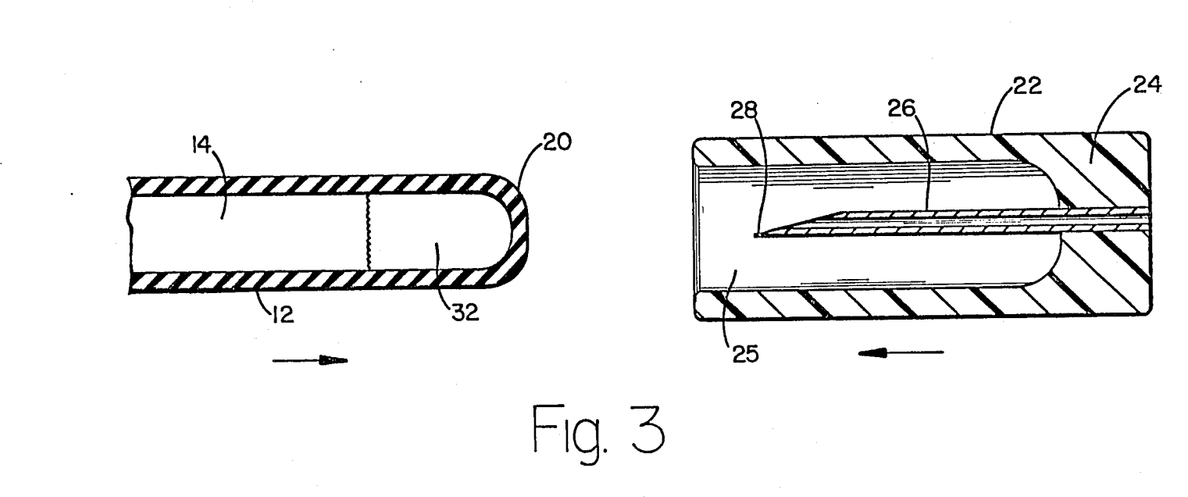
FIGS. 3-6 are cross-sectional views illustrating the sequence of positioning the air purging member on the distal end of the catheter to purge air from the lumen of the catheter and removing the air purging member to retain liquid in the catheter for the desired activity.

Before turning to the operation and use of the air purging member on the instant catheter assembly, another detail of catheter tube 12 should be pointed out. So that compatibility exists between catheter tube 12 and air purging member 22, distal end 20 of the catheter tube should be penetrable or pierceable by cannula point 28. Since most catheters of the type under discussion here are fabricated from flexible or resilient material, there is normally no difficulty in rendering distal end 20 of the tube pierceable. In addition to being penetrable, however, distal end 20, for purposes of the present invention should also be sealable so that liquid within lumen 14 may be retained therein after cannula 26 is removed or withdrawn from distal end 20. A mechanism for providing this sealing effect is preferably a self-sealing plug 32 within lumen 14 at distal end 20 of the tube, as illustrated in FIG. 3. Plug 32 is preferably an elastomeric material such as rubber, silicone rubber, or the like, which, while penetrable by cannula 26, is self-sealing after the cannula has been withdrawn. In addition to its self-sealing features, plug 32 could provide some stiffness to the distal end of the catheter tube in those instances where the tube is thin and very flexible. Further, the plug may add columnar strength to the distal end of the catheter tube. After the cannula is withdrawn from plug 32 the self-sealing nature of the material provides a substantially liquid-tight seal so that liquid within lumen 14 cannot escape from the distal end of the tube.

Figure 4:
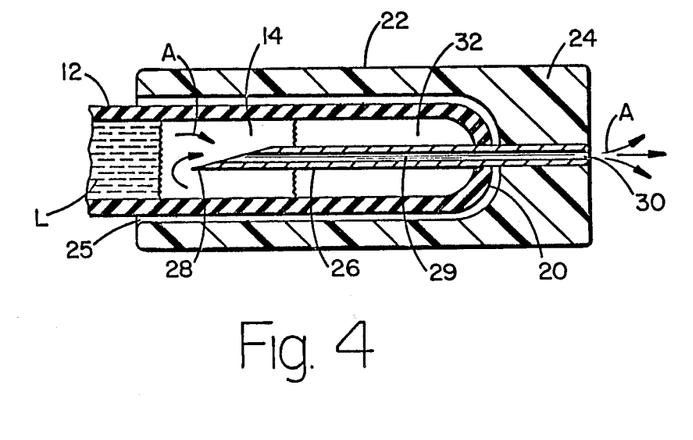

FIGS. 3-6 illustrate the use of the present catheter assembly in sequential steps of operation. In FIG. 3, catheter tube 12 and air purging member 22 are shown separated prior to use of the catheter on a patient. At this stage, lumen 14 normally has no filling liquid therein, only air. As pointed out above, removal of the air within lumen 14 is the aim of the present invention, since air inside the catheter tube might cause an air embolus in a patient's blood vessel if the catheter tube or balloon should fail. Air purging member 22 is thus slid over distal end 20 of catheter tube 12 so that recess 25 surrounds the distal end. As this sliding step occurs, sharp point 28 of cannula 26 penetrates distal end 20 and plug 32 until point 28 enters lumen 14 of the tube. When this position is achieved passageway 29 of cannula 26 is in fluid communication with lumen 14 of the tube. A temporary fluid path is thus provided between the lumen of the catheter tube and the outside environment through opening 30 at the end of purge member 22. The positioning of the air purging member on the distal end of the catheter tube is illustrated in FIG. 4.

Figure 5:
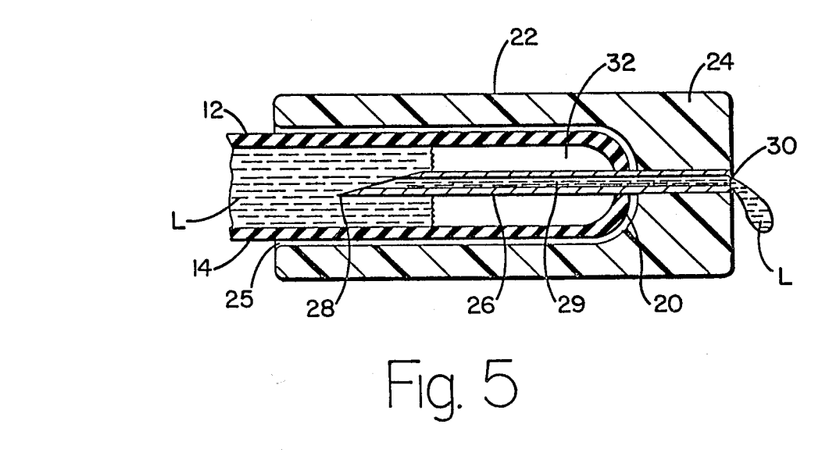

FIG. 4 also illustrates the introduction of liquid L into lumen 14. Although not illustrated in FIG. 4, filling liquid has been introduced into lumen 14 via connector 16 at the proximal end of tube 12. As liquid L travels toward the distal end of the catheter tube and cannula 26, air (designated by the arrows and letter A) inside lumen is forced into passageway 29 of cannula 26. As air A is displaced from lumen 14 it travels through passageway 29 and exits opening 30 for purging into the outside environment. Eventually, substantially all air is displaced from lumen 14 and filling liquid L then enters passageway 29. This occurrence is illustrated in FIG. 5. The user of the catheter assembly is able to visualize the droplets of liquid L emerging from opening 30 at the end of air purging member 22. When this occurs, substantially all air has been removed from the lumen of the catheter tube. The catheter tube is now filled with liquid for purposes of activating the catheter for the desired activity in the body passage.

Figure 6:
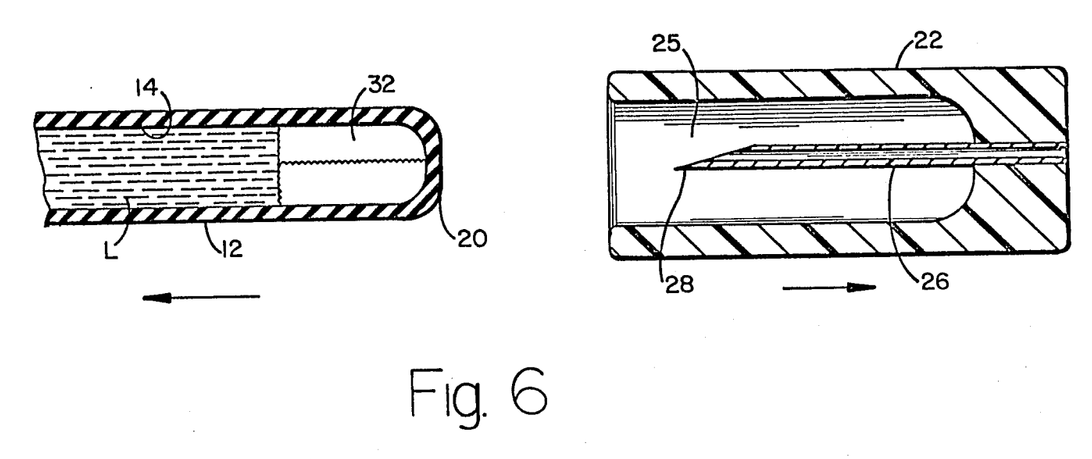

After liquid L emerges from opening 30, the introduction of additional liquid into the lumen is terminated. Then, air purging member 22 is removed from distal end 20 of the catheter tube by a sliding action. Removal of air purging member 22 from distal end 20 is illustrated in FIG. 6. After cannula 26 has been withdrawn from the distal end of the tube, plug 32 seals the opening created by the cannula due to its self-sealing properties. As a result, liquid L is retained within the lumen of the catheter tube. Air purging member 22 is preferably discarded after a single use. Catheter tube 12, filled with liquid, is then ready for use. The liquid-filled catheter tube is inserted into a body passage whereupon the desired activity therein is performed. Some of such desired activities in the body passage have been described above.

It is apparent that the air purging member of the present invention permits the creation of a fluid path between the lumen of the catheter tube and the outside environment. In a sense, the air purging member may be viewed as a valve mechanism which is operative to allow air to pass out of the lumen when the valve is open. When the valve is closed, no air or liquid inside the lumen of the catheter may escape. Thus, various valve mechanisms for the purposes herein described fall within the purview of the present invention.

Although the catheter tube and air purging member of the present invention may be provided to the user as separate elements, it is preferred that they be provided in a single kit or package. In such a kit, the size and shape of the air purging member can be matched for a proper sliding fit over the distal end of the catheter tube. The catheter tube and the air purging member, while separated within the kit or package, are readily assembled by the user in accordance with the steps described above, or the tube and the air purging member may be preassembled in the package.

Figure 7:
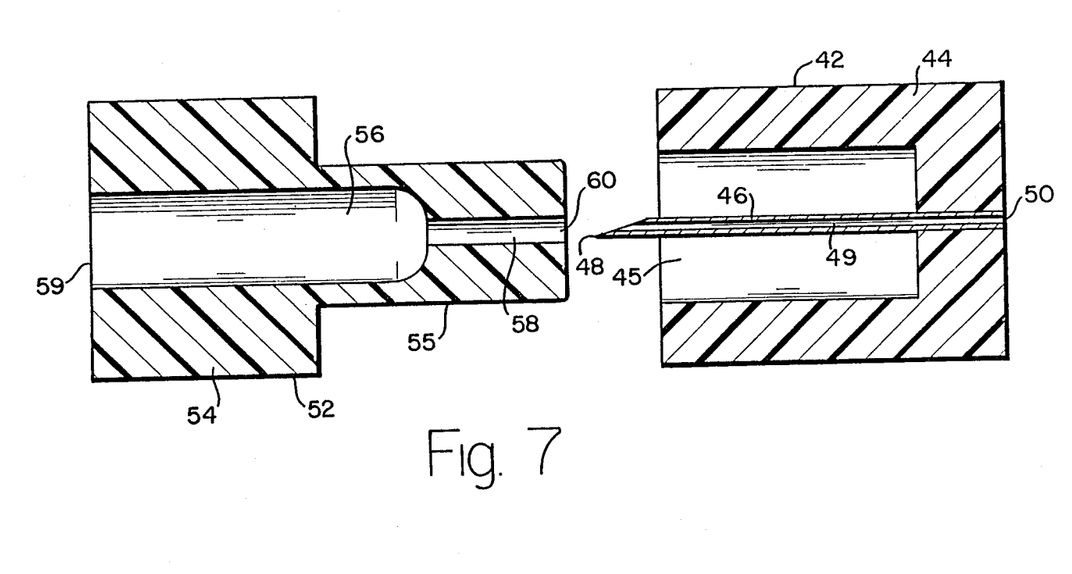
FIG. 7 is an enlarged cross-sectional view of an alternative embodiment of the air purging means including an air purging element and an adapter for positioning on the distal end of the catheter.
Figure 8:
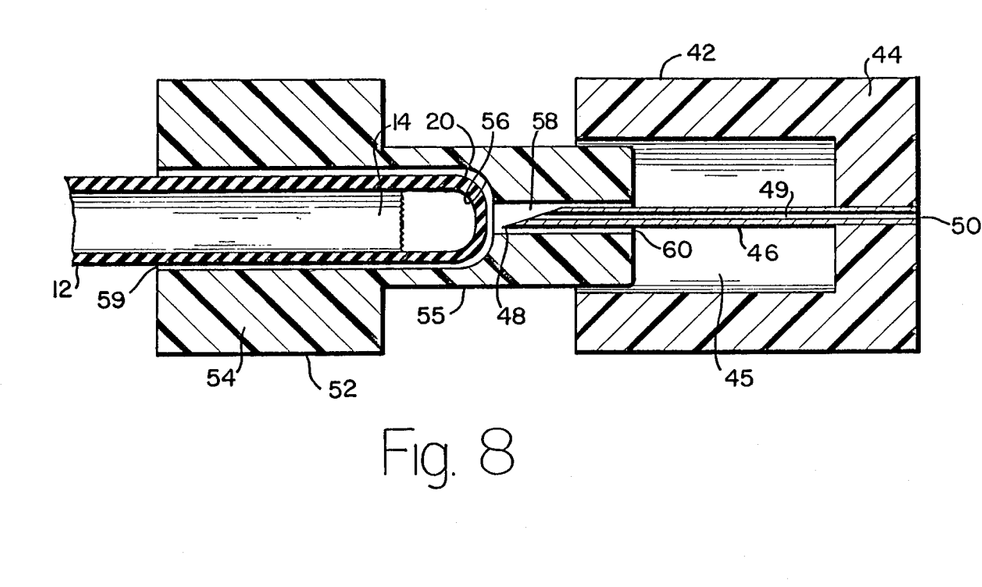
FIGS. 8 and 9 are enlarged cross-sectional views illustrating the sequence of positioning the adapter of FIG. 7 on the distal end of the catheter and positioning the air purging element onto the adapter in order to purge air from the lumen of the catheter in accordance with the principles of the present invention.
Figure 9:
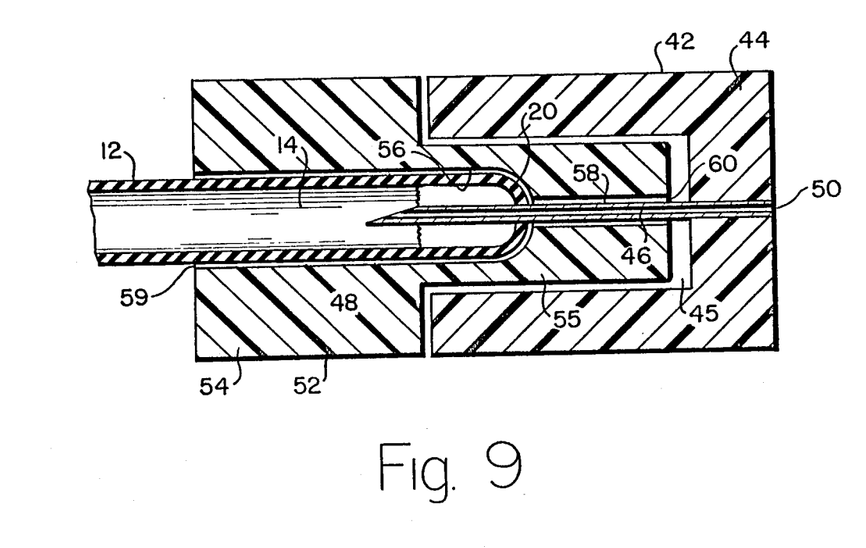

Different variations of the catheter purging mechanism are contemplated in accordance with the present invention. One such alternative embodiment is illustrated in FIG. 7, while FIGS. 8 and 9 show the sequence of employing this alternative embodiment for purging air from the catheter tube. The embodiment of FIG. 7 is useful in those situations where the cannula is relatively long and could be bent or deflected before its insertion into the distal end of the catheter tube. Thus, in this embodiment an adapter is provided to facilitate the insertion of the cannula into the distal end of the catheter tube as will be described.

An air purging element 42 is in many respects similar to air purging member 22 described above, and includes a preferably cylindrically-shaped body 44 into which a cavity 45 extends. Mounted within body 44 and extending through cavity 45 is a hollow cannula 46, which includes a sharp point 48 and a passageway 49 extending therethrough. Passageway 49 terminates in an opening 50 at the end of body 44 so that air purged from the catheter tube may pass into the open environment.

Adapter 52 is comprised of a first body portion 54 and a second body portion 55. It preferred that body portion 55 be of a size and shape so that it meets with the configuration of cavity 45 in purging element 42. To this end, it is preferred that body portion 55 be of a size and shape to slidably fit within cavity 45 once purging elements 42 and adapter 52 are joined together. It can be seen that first body portion 54 includes an elongate recess 56 extending partially through adapter 52. Recess 56 is preferably shaped and sized so as to slidably receive the distal end of the catheter tube from which air is to be purged. Recess 56 terminates in an opening 59 through which the distal end of the catheter is placed so as to be received within the recess. In fluid communication with recess 56 is a passageway 58 which terminates in an opening 60 at the end of second body portion 55. Passageway 58 is sized as to be slightly larger than the outside diameter of cannula 46.

Before use of this embodiment of the instant invention, it is preferred that the two main elements described herein, i.e., purging elements 42 and adapter 52 be included in a kit or package with the catheter tube. In this kit or package, the size and shape of the air purging element and the adapter may be matched for proper sliding fit of the adapter over the catheter tube and for the sliding fit between the adapter and the air purging element.

FIGS. 8 and 9 illustrate the use of the embodiment of the invention shown in FIG. 7. Turning first to FIG. 8, it can be seen that purging element 42 and adapter 55, initially separated, have been joined by a body portion 55 slidably engaging body 44 surrounding cavity 45. When body portion 55 slides into cavity 45, it can be seen that cannula 46 is guided first through opening 60 and then into passageway 58. This arrangement serves to keep the cannula aligned in a straight axis so that the cannula is not bent or deflected prior to entering the distal end of the catheter tube.

In FIG. 9, adapter 52 is positioned in virtual butting arrangement with purging element 42 so that body portion 55 of the adapter is positioned well within cavity 45 of the purging element. In this arrangement, cannula 46 is maintained in axial alignment within passageway 58 of body portion 55. Sharp point 48 of the cannula has penetrated distal end 20 of catheter tube 20 whereby cannula 46 is in fluid communication with lumen 14 of the catheter tube. Air is purged from within the lumen of the catheter tube in similar fashion to the embodiment described above. Air from lumen 14 travels through cannula 46 and exits into the environment through opening 50 at the end of air purging element 42.

Thus, the present invention provides a catheter assembly with an air purging or valving feature which provides a facile and efficient technique for purging air from a catheter or like instrument. The components of the invention are straightforward to manufacture, and the use of the invention is convenient.

What is claimed is:

1. A catheter assembly comprising:
   a flexible tube having a liquid-receiving lumen therethrough, said tube having a proximal end for receiving liquid into said lumen and having a closed, but penetrable, distal end; and
   air purging means including a body removably engaged to the distal end of said tube and a hollow cannula extending through said body and said distal end in fluid communication with said lumen, said cannula providing a path to the outside environment for purging air from said lumen as liquid is introduced into said lumen, said cannula supported by and connected to a purging element, said distal end being sealable to retain liquid within said lumen after said body is removed from the tube, said body and said element being slidably engaged to each other.

2. The assembly of claim 1 wherein said body includes a recess therein shaped to slidably fit over the distal end of said tube.

3. The assembly of claim 2 wherein said body includes a passageway for said cannula, said passageway being in communication with said recess.

4. The assembly of claim 3 wherein said element includes a cavity for slidably receiving a portion of said body.

5. The assembly of claim 1 wherein said body and said element are completely separable from each other.

6. A catheter assembly kit comprising:
   a flexible catheter tube having a lumen and means for introducing liquid into said lumen, said tube having a closed distal end with means for access into said lumen;
   an air purging element including a body with a hollow cannula extending therethrough for communication with said lumen for purging air from the lumen of said tube by providing a fluid path between said lumen and the outside environment thereof; and
   an adapter for removable engagement to the distal end of said tube and to the body of said purging element and including a passageway therethrough for the slidable passage of said cannula, said adapter to provide operative association between said access means and said element to facilitate the creation of said fluid path.

* * * * *